(12) United States Patent
Huang et al.

(10) Patent No.: US 8,453,520 B2
(45) Date of Patent: Jun. 4, 2013

(54) HINGE DURABILITY TESTING DEVICE

(75) Inventors: Teng-Tsung Huang, New Taipei (TW);
Guo-Jun Yu, Shenzhen (CN);
Yong-Bing Hu, Shenzhen (CN);
Zhang-Sheng Yan, Shenzhen (CN)

(73) Assignees: Hong Fu Jin Precision Industry (ShenZhen) Co., Ltd., Shenzhen (CN);
Hon Hai Precision Industry Co., Ltd., New Taipei (TW)

( * ) Notice: Subject to any disclaimer, the term of this patent is extended or adjusted under 35 U.S.C. 154(b) by 79 days.

(21) Appl. No.: 13/207,172

(22) Filed: Aug. 10, 2011

(65) Prior Publication Data
US 2012/0186359 A1 Jul. 26, 2012

(30) Foreign Application Priority Data
Jan. 24, 2011 (CN) ...................... 2011 2 0022120 U

(51) Int. Cl.
*G01L 3/02* (2006.01)
*G01N 3/02* (2006.01)
*G01N 3/22* (2006.01)

(52) U.S. Cl.
USPC .......... 73/862.191; 73/856; 73/865.3; 73/847

(58) Field of Classification Search
USPC ............... 73/847, 848, 862.191, 862.08, 798, 73/865.3
See application file for complete search history.

(56) References Cited

U.S. PATENT DOCUMENTS

| 2,300,288 | A | * | 10/1942 | Hullhorst | 73/862.191 |
|---|---|---|---|---|---|
| 3,508,806 | A | * | 4/1970 | Hall | 359/393 |
| 6,571,969 | B2 | * | 6/2003 | Larbaletier | 211/150 |
| 6,826,963 | B2 | * | 12/2004 | Liu et al. | 73/798 |
| 8,291,774 | B2 | * | 10/2012 | Huang et al. | 73/862.191 |
| 8,302,488 | B2 | * | 11/2012 | Hsu et al. | 73/856 |
| 8,316,720 | B2 | * | 11/2012 | Huang et al. | 73/847 |
| 2004/0065155 | A1 | * | 4/2004 | Liu et al. | 73/798 |
| 2005/0241450 | A1 | * | 11/2005 | Schwartz | 83/446 |
| 2012/0024078 | A1 | * | 2/2012 | Huang et al. | 73/847 |

* cited by examiner

*Primary Examiner* — Lisa Caputo
*Assistant Examiner* — Jonathan Dunlap
(74) *Attorney, Agent, or Firm* — Altis Law Group, Inc.

(57) ABSTRACT

A hinge durability testing device for testing the durability of a hinge hinging a cover with a main body, includes a main body holder holding the main body, a cover holder holding the cover, the cover holder hinged to the main body holder, the cover holder comprising two support rods and a connecting rod; each support rod comprising a first surface facing the other support rod, and a second surface adjacent to the first surface; each first surface defining a first sliding groove, and each second surface defining a second sliding groove comminuting with corresponding first sliding groove; two connecting elements, each connecting element located on one end of the connecting rod and slidably mounted in one of the first sliding grooves; a plurality of locking elements, each locking element retained on one of the connecting elements and slidably mounted in one of the second sliding grooves.

13 Claims, 3 Drawing Sheets

HINGE DURABILITY TESTING DEVICE

BACKGROUND

1. Technical Field

This disclosure relates to hinge durability testing devices, particularly to a hinge durability testing device for testing a hinges lifespan.

2. Description of Related Art

Some electronic devices are flip type devices, which include a cover, a main body and a hinge rotatably coupling the cover and the main body. The hinge is used to open and close the cover relative to the main body, so the durability of the hinge is an important parameter of the electronic device. Thus, the durability of the hinge must be tested in the manufacture procedure. To test the durability of the hinge, a test device is used. The test device typically includes a cover holder used to hold the cover and a main body holder used to hold the main body. The cover holder rotates relative to the main body holder causing the cover to open and close relative to the main body, as a result, the durability of the hinge is tested. However, typical test device cannot steadily hold the cover, which makes it difficult to get a precise value of the durability of the hinge.

Therefore, there is a room for improved in the art.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the exemplary hinge durability testing device. Moreover, in the drawings like reference numerals designate corresponding parts throughout the several views. Wherever possible, the same reference numbers are used throughout the drawings to refer to the same or like elements of an embodiment.

DETAILED DESCRIPTION

Figure 1:
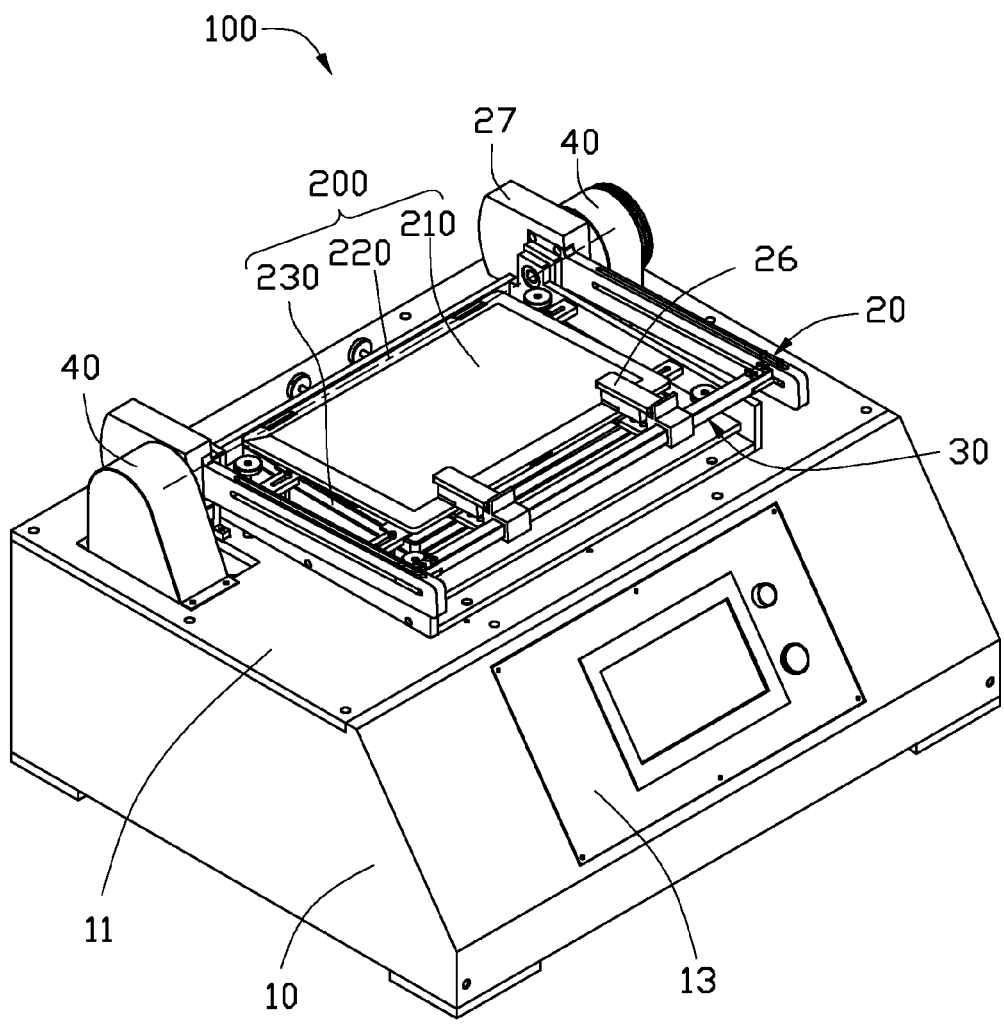
FIG. 1 is a schematic view of an exemplary embodiment of a hinge durability testing device in a first state.

Referring to FIG. 1, an exemplary embodiment of a hinge durability testing device 100 for testing the durability of a hinge 220 of an electronic device 200 is shown. The hinge durability testing device 100 includes a chassis 10, a cover holder 20, a main body holder 30 and two driving mechanisms 40. The electronic device 200 includes a cover 210 and a main body 230, both of which are hinged by the hinge 220. The cover holder 20 is used to hold the cover 210. The main body holder 30 is used to hold the main body 230. The driving mechanism 40 is used to drive the cover holder 20 to rotate relative to the main body holder 30, causing the cover 210 to rotate relative to the main body 230.

The chassis 10 includes a platform 11, on which the cover holder 20 and the main body holder 30 are mounted. The chassis 10 further includes a control panel 13, e.g., a touch panel, controlling the openings and closings of the cover holder 20 relative to the main body holder 30.

Figure 2:
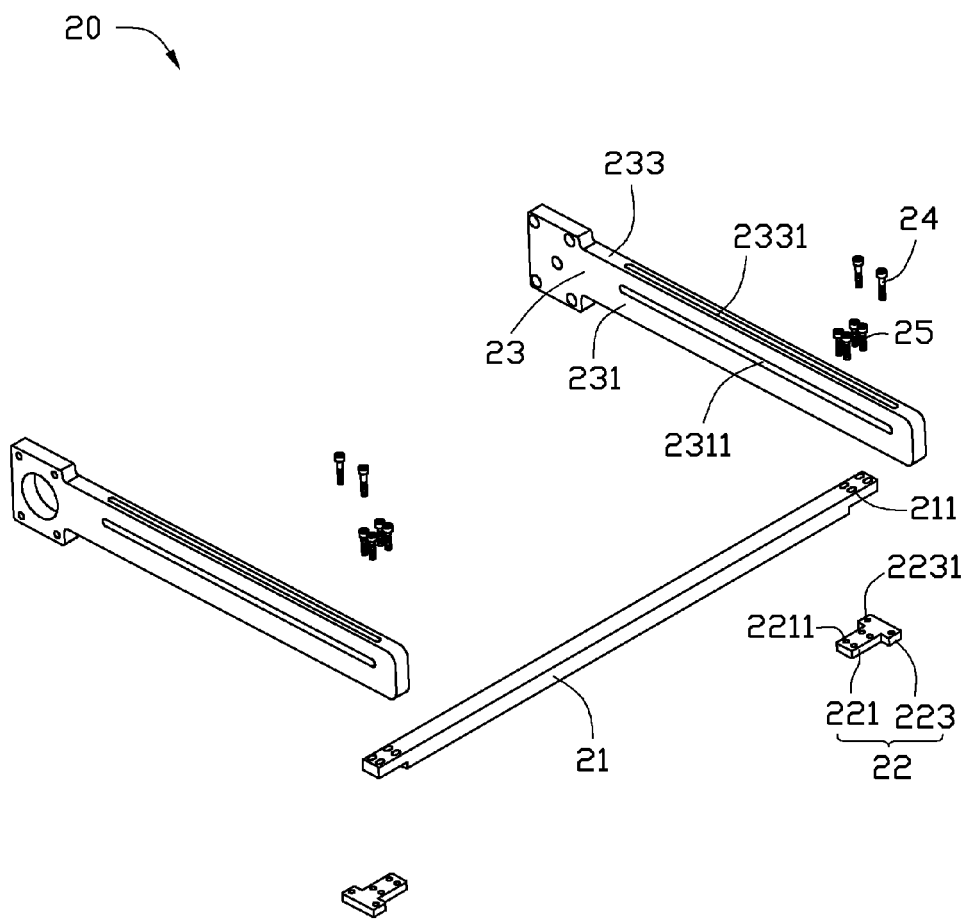
FIG. 2 is an exploded view of a cover holder of the hinge durability testing device shown in FIG. 1.

Referring to FIG. 2, the cover holder 20 is substantially U-shaped, includes a connecting rod 21, two connecting elements 22, two support rods 23 respectively and movably mounted on the connecting element 22. A plurality of locking elements 24, a plurality of screws 25, at least one holding element 26 (shown in FIG. 1) and two mounting blocks 27 (shown in FIG. 1).

The connecting rod 21 has a plurality of unthreaded mounting holes 211 defined near the two ends. Each screw 25 is located and can move longitudinally in one of the unthreaded mounting holes 211. Each connecting element 22 includes a first connecting portion 221 and a second connecting portion 223 protruding from the first connecting portion 221. The first connecting portion 221 defines a plurality of threaded holes 2211. One screw 25 is screwed in each hole 2211, to retain the connecting rod 21 on the connecting elements 22. When the screws 25 are loosened, the connecting elements 22 can move longitudinally relative to the connecting rod 21 as the screws 25 move in their corresponding unthreaded mounting holes 211. Each second connecting portion 223 defines a plurality of retaining holes 2231, each of which holds one of the locking elements 24.

Each support rod 23 includes a first surface 231 facing the other support rod 23, and a second surface 233 adjacent to the first surface 231. Each support rod 23 has a first sliding groove 2311 defined in the first surface 231, in which one of the second connecting portions 223 is slidably located. Each support rod 23 defines a second sliding groove 2331 in the second surface 233 and perpendicular and communicating with a corresponding first sliding groove 2311. The locking elements 24 are slidably located in the second sliding grooves 2331. In this exemplary embodiment, the locking elements 24 are screws. One end of each locking element 24 is screwed in one of the retaining holes 2231, the other end is bigger than the second sliding grooves 2331 to prevent the support rods 23 from separation from the connecting rod 21. To adjust the position between the connecting rod 21 and the support rods 23, the connecting elements 22 slide in the first sliding grooves 2311 and the locking elements 24 slide in the second sliding grooves 2331. In addition, because the locking elements 24 slide in the second sliding grooves 2331, the connecting rod will not incline when sliding relative to the support rods 23.

Figure 3:
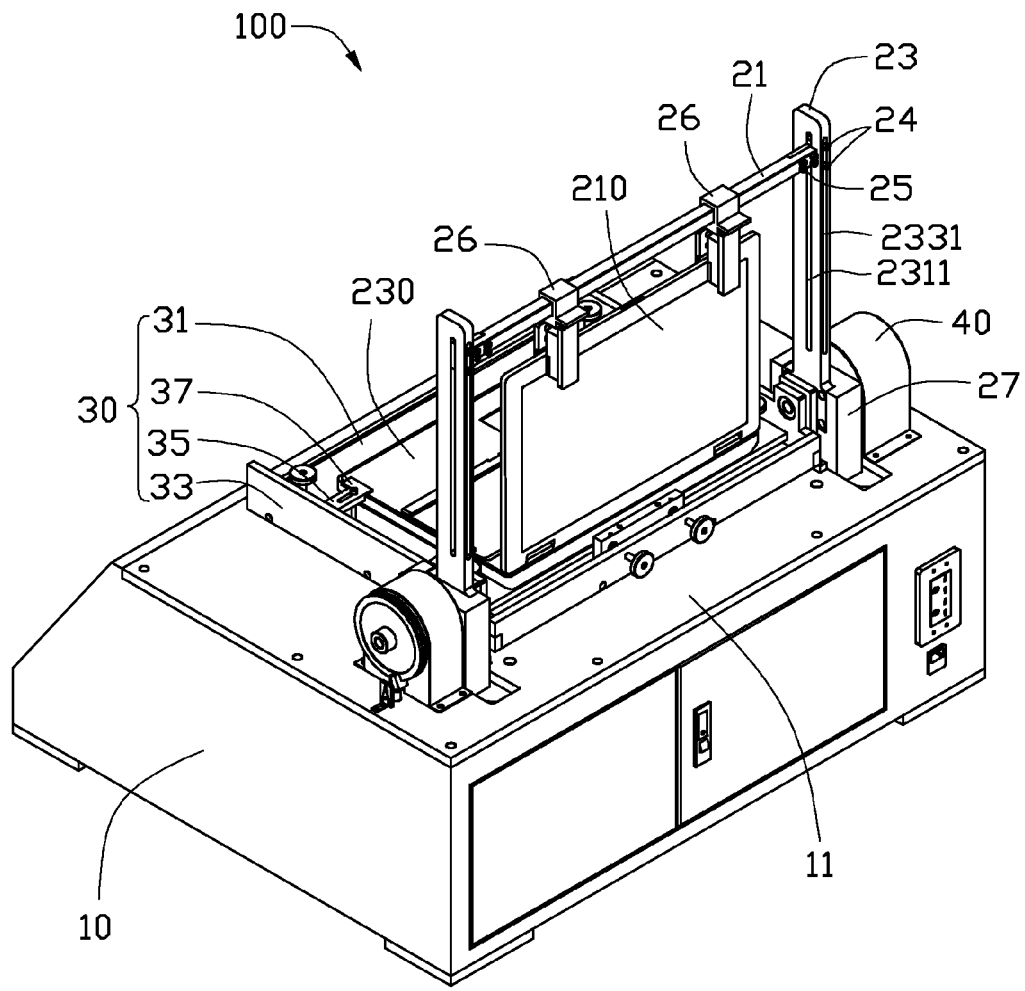
FIG. 3 is a schematic view of the hinge durability testing device in a second state.

Referring to FIG. 3, the holding element 26 is mounted on the connecting rod 21. The holding element 26 holds the cover 210 so the cover 210 can rotate with the connecting rod 21. Each mounting block 27 is located at a distal end of one of the support rods 23 and hinged to one of the driving mechanisms 40. The driving mechanisms 40 drive the mounting blocks 27 and the support rods 23 to rotate.

The main body holder 30 includes a base 31 mounted on the platform 11, two sidewalls 33 located at opposite sides of the base 31, a plurality of securing plates 35 protruding from the sidewall above the base 31, a plurality of screws 37 equal in number to the number of securing plates 35. The base 31 is used to support the main body 230. In this exemplary embodiment, each sidewall 33 has two securing plates 35. The main body 230 is located between the securing plates 35 and the base 31, and secured by the screws 37 so the main body 230 is held on the main body holder 30.

To test the hinge of the electronic device 200, the cover 210 is held by the holding elements 26 the main body 230 is secured between the base 31 and the securing plates 35. Then, the driving mechanisms 40 drive the cover holder 20 to open and close relative to the main body holder 30 so the cover 210 opens and closes relative to the main body 230 until a predetermined durability of the hinge 220 is reached. Additionally, the locking elements 24 can be loosened and then the connecting rod 21 slides relative the support rods 23 to adjust the cover holder 20, to test another electronic device 200 which has a different size from the first electronic device 200.

It is to be further understood that even though numerous characteristics and advantages of the exemplary embodiments have been set forth in the foregoing description, together with details of structures and functions of various embodiments, the disclosure is illustrative only, and changes may be made in detail, especially in matters of shape, size, and arrangement of parts within the principles of the exemplary invention to the full extent indicated by the broad general meaning of the terms in which the appended claims are expressed.

What is claimed is:

1. A hinge durability testing device for testing the durability of a hinge hinging a cover with a main body, the hinge durability testing device comprising:
   a main body holder for holding the main body;
   a cover holder for holding the cover, the cover holder hinged to the main body holder, the cover holder comprising two support rods and a connecting rod; each support rod comprising a first surface facing the other support rod, and a second surface connected to the first surface; each first surface defining a first sliding groove, and each second surface defining a second sliding groove comminuting with one corresponding first sliding groove;
   two connecting elements, each connecting element mounted on one end of the connecting rod and slidably received in one of the first sliding grooves;
   a plurality of locking elements, each locking element slidably received in one of the second sliding grooves and retained on one of the connecting elements in the corresponding first sliding groove for preventing the connecting rod from separation from the support rods.

2. The hinge durability testing device of claim 1, wherein the cover holder further comprises a plurality of screws, the connecting rod has a plurality of unthreaded mounting holes defined near two ends thereof, each screw is movably located in one of the unthreaded mounting holes, each connecting element defines a plurality of threaded holes, in which the screws are screwed.

3. The hinge durability testing device of claim 1, wherein each connecting element defines a plurality of retaining holes, one end of each locking element is screwed in one of the retaining holes, the other end of each locking element is bigger than the second sliding groove and protrudes from the second surface of each support rod.

4. The hinge durability testing device of claim 3, wherein the locking elements are screws.

5. The hinge durability testing device of claim 1, wherein the cover holder includes at least one holding element mounted on the connecting rod, the holding element is used to hold the cover.

6. The hinge durability testing device of claim 1, wherein the main body holder includes a base used to support the main body, two sidewalls located at opposite sides of the base, a plurality of securing plates protruding from the sidewall above the base, a plurality of screws equal in number to the number of securing plates; the main body is located between the securing plates and the base, and secured by the screws so the main body is held on the main body holder.

7. The hinge durability testing device of claim 1, further comprising two driving mechanism; the cover holder further comprising two mounting blocks, each mounting block hinged to one of the driving mechanism and retained on a distal end of one of the support bars; the driving mechanisms drive the mounting block and the support bars to rotate.

8. A hinge durability testing device for testing the durability of a hinge hinging a cover with a main body, the hinge durability testing device comprising:
   a main body holder for holding the main body;
   a cover holder for holding the cover, the cover holder hinged to the main body holder, the cover holder comprising two support rods and a connecting rod releasably mounted between the support rods; each support rod comprising a first surface facing the other support rod, and a second surface adjacent to the first surface; each first surface defining a first sliding groove, and each second surface defining a second sliding groove comminuting with a corresponding first sliding groove;
   two connecting elements, each connecting element retained on one end of the connecting rod and slidably mounted in one of the first sliding grooves;
   a plurality of locking elements, each locking element passing through corresponding second sliding groove and screwed to a corresponding connecting element to retain the connecting rod to the support bars;
   wherein after the locking elements are loosened, the connecting elements slide in the first sliding grooves and the locking elements slide in the second sliding grooves so the connecting rod slides relative the support rods to adjust the cover holder;
   wherein the cover holder further comprises a plurality of screws, the connecting rod has a plurality of unthreaded mounting holes defined near two ends thereof, each screw is movably located in one of the unthreaded mounting holes, each connecting element defines a plurality of threaded holes, in which the screws are screwed.

9. The hinge durability testing device of claim 8, wherein each connecting element defines a plurality of retaining holes, one end of each locking element is screwed in one of the retaining holes, the other end of each locking element is bigger than the second sliding groove and protrudes from the second surface of each support rod.

10. The hinge durability testing device of claim 9, wherein the locking elements are screws.

11. The hinge durability testing device of claim 8, wherein the cover holder includes at least one holding element mounted on the connecting rod, the holding element is used to hold the cover.

12. The hinge durability testing device of claim 8, wherein the main body holder includes a base used to support the main body, two sidewalls located at opposite sides of the base, a plurality of securing plates protruding from the sidewall above the base, a plurality of screws equal in number to the number of securing plates; the main body is located between the securing plates and the base, and be secured by the screws so the main body is held on the main body holder.

13. The hinge durability testing device of claim 8, further comprising two driving mechanism; the cover holder further comprising two mounting blocks, each of which is hinged to one of the driving mechanism and retained on a distal end of one of the support bars; the driving mechanisms drive the mounting blocks and the support bars to rotate.

* * * * *